United States Patent [19]

Fogerty

[11] Patent Number: 5,662,471
[45] Date of Patent: Sep. 2, 1997

[54] ORTHODONTIC SHIELD AND METHOD OF MAKING

[76] Inventor: Bruce A. Fogerty, 4419 Rawlins, Dallas, Tex. 75219

[21] Appl. No.: 434,772

[22] Filed: May 4, 1995

[51] Int. Cl.⁶ ............................................. A61C 3/00
[52] U.S. Cl. ................................................ 433/22; 433/2
[58] Field of Search .......................... 433/2, 6, 22, 24; 128/862

[56] References Cited

U.S. PATENT DOCUMENTS

| | | | |
|---|---|---|---|
| 3,224,443 | 12/1965 | Monaghan | 128/862 |
| 3,372,484 | 3/1968 | Mumaw | 433/2 |
| 3,379,193 | 4/1968 | Monaghan | 433/6 |
| 4,512,740 | 4/1985 | Kurz | 433/6 |
| 4,559,013 | 12/1985 | Amstutz et al. | 433/6 |
| 4,687,441 | 8/1987 | Klepacki | 433/8 |
| 4,913,654 | 4/1990 | Morgan et al. | 433/8 |
| 4,954,080 | 9/1990 | Kelly et al. | 433/8 |
| 5,037,296 | 8/1991 | Karwoski | 433/22 |
| 5,083,919 | 1/1992 | Quach | 433/24 |
| 5,160,260 | 11/1992 | Chang | 433/2 |

Primary Examiner—Cary E. O'Connor
Attorney, Agent, or Firm—Michael A. O'Neil; Russell N. Rippamonti

[57] ABSTRACT

An orthodontic shield comprising a strip of plastic material having a predetermined color and having predetermined length, width, and thickness dimensions. The strip of plastic material is heated sufficiently to render it malleable to the touch, and the strip of plastic material is then engaged with an orthodontic appliance and the adjacent tooth surfaces of a patient to conform the strip of plastic material to the configuration of the orthodontic appliance and the adjacent tooth surfaces. The strip of plastic material is allowed to cool within the mouth of the patient, whereby the orthodontic shield is retained in the mouth of the patient during daily activities such as diction and eating, but is readily removable therefrom for cleaning, etc.

8 Claims, 2 Drawing Sheets

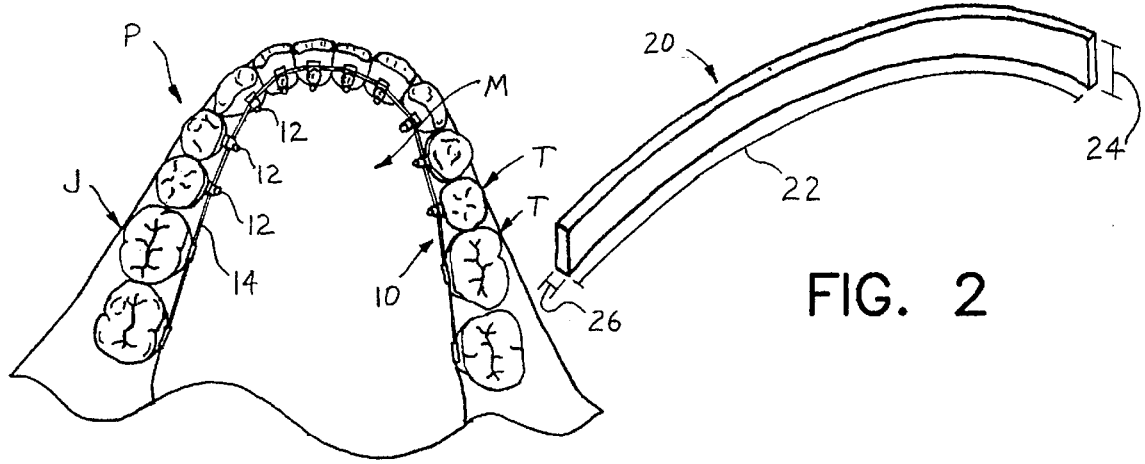
FIG. 2
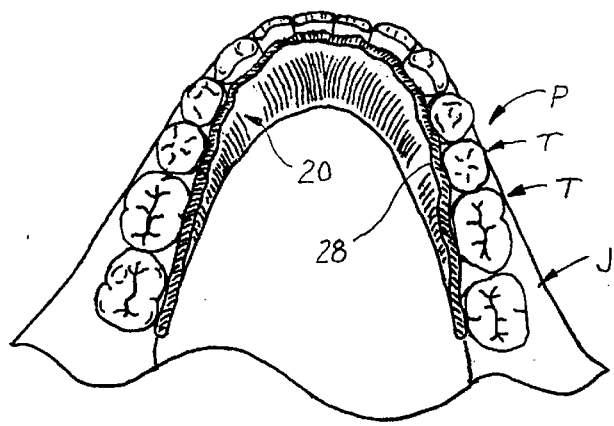
FIG. 1
PRIOR ART
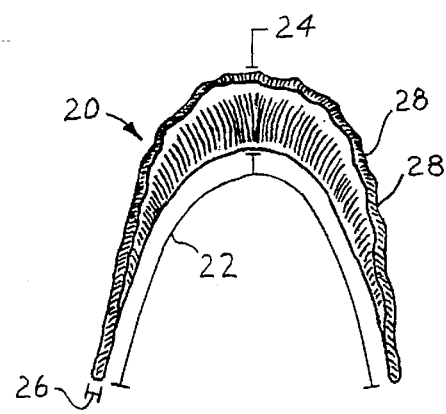
FIG. 4
FIG. 3

ORTHODONTIC SHIELD AND METHOD OF MAKING

TECHNICAL FIELD

This invention relates generally to orthodontia, and more particularly to a shield useful during orthodontic procedures to provide increased patient comfort and convenience.

BACKGROUND OF THE INVENTION

As is generally known, the practice of orthodontia involves the selected application of predetermined forces to the teeth of a patient, thereby physically relocating the teeth into desired orientations.

More specifically, the typical orthodontic procedure involves the mounting of orthodontic appliances, commonly referred to in the vernacular as braces, on the teeth of the patient for use in applying tooth relocating forces thereto. Typically, brackets are mounted on the teeth either directly by bonding or indirectly by mounting the brackets on tooth encircling bands and then cementing the bands to the teeth. Buccal tubes are mounted on bands which are secured to the molars of the patient and are used to support archwires which extend adjacent the teeth along generally arcuate paths. Ligatures, which may comprise either stainless steel wires or elastomeric members, are secured between the brackets and the archwires to apply tooth moving forces.

Despite their beneficial results, orthodontic procedures are generally considered to be both uncomfortable and inconvenient. For example, when orthodontic appliances are mounted on the labial or outwardly facing surfaces of the teeth they are positioned to engage and sometimes snag the inside surfaces of the lips of the patient. Even worse, when orthodontic appliances are mounted on the inwardly facing or lingual surfaces of the teeth they tend to interfere with the tongue of the patient during diction and eating. In either case, orthodontic appliances tend to clog with food particles during chewing and are notoriously hard to clean after clogging occurs.

SUMMARY OF THE INVENTION

The present invention comprises a orthodontic shield which overcomes the foregoing and other problems long since associated with the prior art. In accordance with the broader aspects of the invention a shield formed from thermoplastic material is positioned to overlay both the teeth of a patient and orthodontic appliances mounted thereon and serves to prevent engagement between the orthodontic appliance and mouth tissues of the patient. The shield is adapted to remain in place both during diction and during chewing, and thereby enhances patient comfort and convenience by preventing painful engagement of the mouth tissues with the orthodontic appliances and by reducing clogging of the orthodontic appliance with food.

In accordance with more specific aspects of the invention, the shield comprises a strip of thermoplastic material having the length and width adapted to cover the orthodontic brackets secured to the teeth of either the upper or the lower jaw of the patient. The shield is preferably formed from a material which is adapted for softening at a relatively low temperature, but which is stable and relatively rigid at approximately 100 degrees Fahrenheit. The shield is softened by emersion in boiling water for a brief period of time, and is then immediately engaged with the orthodontic appliance and the adjacent tooth surfaces to be protected. Upon the application of moderate pressure the shield is conformed into engagement with the orthodontic appliance and the tooth surfaces, and upon cooling comprises a structure which "snaps" into place and remains in place as long as desired, but which is readily disengageable from the mouth of the patient for cleaning, etc. When in place the shield fully protects the mouth tissues of the patient from engagement with the brackets and other apparatus used in the orthodontic procedure, and simultaneously substantially prevents clogging of the orthodontic appliance with food particles.

BRIEF DESCRIPTION OF THE DRAWINGS

A more complete understanding of the present invention may be had by reference to the following Detailed Description when taken in conjunction with the accompanying Drawings, wherein:

FIG. 1 is an illustration of part of the mouth of a patient having an orthodontic appliance mounted therein;

FIG. 2 is an illustration of the orthodontic shield of the present invention prior to the application thereof to the mouth of a patient;

FIG. 3 is an illustration similar to FIG. 1 showing the orthodontic shield of the present invention applied to and positioned in the mouth of a patient;

FIG. 4 is an illustration of an orthodontic shield comprising a first embodiment of the present invention;

DETAILED DESCRIPTION

Figure 5:
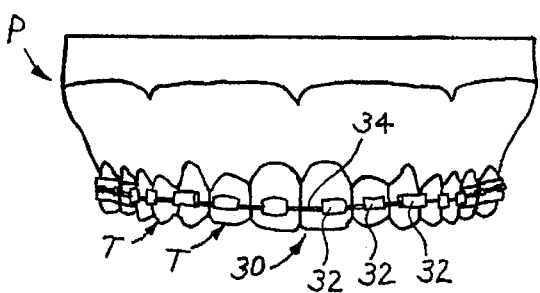
FIG. 5 is an illustration of part of the mouth of a patient having an orthodontic appliance mounted therein.

Referring now to the Drawings, and particularly to FIG. 1, there is shown the upper jaw J comprising part of the mouth M of a patient P. The jaw J comprises a plurality of teeth T which are arranged, as usual, in a generally semi-circular arch. Those skilled in the art will appreciate the fact that in FIG. 1 the teeth T of the jaw J are illustrated in a "straight" condition. In the practice of the science of orthodontia, the teeth of the patient are initially misaligned and are moved by the selective application of tooth positioning forces until they are "straight" as illustrated in FIG. 1

FIG. 1 further illustrates an orthodontic appliance 10 secured inside the mouth M of the patient P and mounted on the teeth T of the jaw J. The orthodontic appliance 10 is mounted on the inside facing or lingual surfaces of the teeth and comprises a plurality of brackets 12, each secured to one of the teeth T, an archwire 14 extending adjacent the lingual surfaces of the teeth and engaging each of the brackets 12 and a plurality of ligatures (omitted for clarity) which are used to secure the brackets 12 to the archwire 14.

Those skilled in the art will appreciate the fact that FIG. 1 comprises a diagrammatical illustration of the orthodontic appliance 10 which is not intended to represent any particular type of orthodontic appliance. The orthodontic shield of the present invention is adapted to use in conjunction with a wide variety of orthodontic appliances comprising any of the various conventional bracket types used in conjunction with any of the various conventional archwire types and secured thereto by one or more of the various ligatures as currently used in the practice of orthodontia.

Referring now to FIG. 2, there is shown an orthodontic shield 20 comprising the present invention prior to the installation thereof in the mouth a patient. The orthodontic shield 20 originally comprises a rectangular, flat strip of thermoplastic material having a predetermined length 22 of about 3¼ inches, having a predetermined width 24 of about ⅝ inch, and having a predetermined thickness 26 of about 1/16 inch. The orthodontic shield 20 may be formed from a variety of thermoplastic materials so long as the selected material meets the following criteria. First, the material must be adapted for long term retention within the mouth of the patient without causing any deleterious result whatsoever to the general health of the patient, to the condition of the teeth of the patient, or to the condition of the other tissues within the mouth of the patient. Second, the material must be relatively rigid at body temperature, but must be malleable at a temperature only somewhat above body temperature so as to be positionable within the mouth of the patient in a malleable state without danger of burning the mouth of the patient. The plastic material used in the manufacture of sports-type mouth guards, model 5522B clear, by the Safe T Guard Corp. of Lakewood, Colo., may be used in the practice of the invention, if desired.

Referring now to FIG. 3, in the practice of the invention the orthodontic shield 20 is initially heated sufficiently to render it malleable to the touch. Preferably, the orthodontic shield 20 is heated by immersing it in boiling water for a period of about 16 seconds. The orthodontic shield 20 is heated to a temperature sufficiently high to render the material thereof malleable, but not to a temperature sufficiently high to be unpleasant to the touch of the patient. In this manner, any danger of burning the mouth of the patient is eliminated.

After the orthodontic shield 20 has been heated sufficiently to render it malleable, it is inserted into the mouth M of the patient P and is engaged with the orthodontic appliance 10 within the mouth M of the patient P. One edge of the length 22 of the orthodontic shield 20 is aligned with the incisal edges of the teeth T upon which the orthodontic appliance 10 is mounted. The inwardly facing or lingual surface of the orthodontic shield 20 is firmly engaged by the fingers of the patient P or the orthodontist, thereby molding the orthodontic shield 20 into the shape of the teeth T of the patient P and the component parts of the orthodontic appliance 10 (not shown).

When the foregoing procedure is followed the orthodontic shield 20 is molded into a shape conforming to the lingual or interior surfaces of the teeth T of the patient P sufficiently to remain firmly located within the mouth of the patient during diction, during eating, and during other normal activities. Because the orthodontic shield 20 is molded into strict conformance with the interior configuration of the teeth T of the patient P and and partially encircling the orthodontic appliance 10 mounted thereon, it is securely retained as a snap fit within the mouth M of the patient, both mechanically and under the action of cohesive forces. Nevertheless, the orthodontic shield 20 is easily removed from the mouth of the patient for cleaning and otherwise by simply lodging a fingernail under the edge of the orthodontic shield.20 and physically dislodging it from the interior surfaces of the teeth and the orthodontic appliance mounted thereon. It has been found in actual practice that when the orthodontic shield 20 is installed in the mouth of a patient in accordance with the foregoing procedures it "snaps" both into and out of engagement of the teeth of the patient, and thus is firmly positioned within the mouth of the patient during daily activities and is adapted for long-term usage without requiring replacement.

An orthodontic shield 20 comprising the present invention and fabricated in accordance with the foregoing procedure is illustrated in FIG. 4. The original dimensions 22, 24 and 26 have not changed to an appreciable degree. However, rather than being flat, as illustrated in FIG. 2, the orthodontic shield 20 is now generally semi-circular in configuration to conform to the interior configuration of the mouth of the patient. The orthodontic shield is further characterized by a plurality of indentions 28, each conforming to the interior configuration of one of the teeth of the patient. The orthodontic shield 20 as shown in FIGS. 3 and 4 further has a configuration which conforms to the shape of the orthodontic appliance 10 (not shown) positioned within the mouth M of the patient P, whereby orthodontic shield 20 "snaps" into place and is thereafter "locked" within the mouth of the patient during daily activities such as diction, eating, etc.

Figure 6:
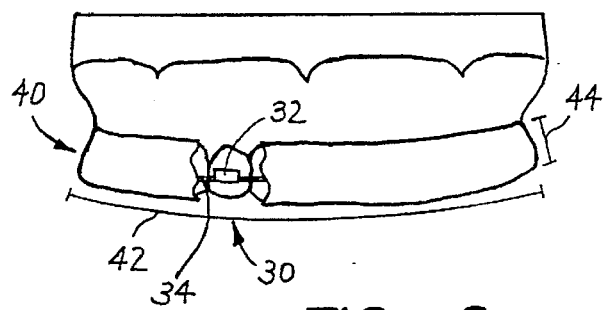
FIG. 6 is an illustration of an orthodontic shield comprising a second embodiment of the present invention mounted in the mouth of a patient.

Referring now to FIGS. 5 and 6, there is shown an orthodontic appliance 30 applied to the outwardly facing or labial surfaces of the teeth T of a patient P. The orthodontic appliance 30 comprises a plurality of brackets 32, each secured to one of the teeth T by conventional means and an archwire 34 extending along an arcuate path adjacent the outwardly facing or labial surfaces of the teeth T. The brackets 32 are secured to the archwire 34 by ligatures (omitted for clarity).

As will be appreciated by those skilled in the art, FIG. 5 comprises a diagrammatic illustration of an orthodontic appliance and is not intended to be representative of any particular type or kind of orthodontic appliance. The orthodontic shield of the present invention is adapted for use with orthodontic appliance comprising any of the various conventional types of brackets used in conjunction with any of the various conventional types of archwires and secured thereto by means of any 0f the various conventional types of ligatures.

Referring to FIG. 6, there is shown an orthodontic shield 40 comprising a second embodiment of the invention. The orthodontic shield 40 originally comprises a flat strip of plastic material shaped somewhat like the orthodontic shield 20 illustrated in FIG. 2, but longer since the dimension comprising the arch extending along the labial surfaces of the teeth is considerably longer than the distance comprising the arch extending along the lingual surfaces of the teeth. In any event, the orthodontic shield 40 has a length dimension 42 sufficient to engage the shield 40 with all of the teeth T of the patient P to which the orthodontic appliance 30 is applied. The orthodontic shield 40 further has a width dimension 44 sufficient to cover at least the exposed surfaces of the orthodontic appliance 36 and preferable the adjacent surfaces of the teeth T of the patient P. The width dimension 44 of the orthodontic shield may be selected in accordance with the preferences of the patient and those of the orthodontist or other professional which is supervising the installation and use of the orthodontic shield 40.

Like the orthodontic shield 20, the orthodontic appliance 40 is preferably formed from a plastic material which is stable at body temperature, but which is malleable at a somewhat elevated temperature which is not sufficiently high to pose a threat of harm to the patient when the orthodontic shield 40 is installed.

Since the orthodontic shield 40 is exposed to view, the color thereof is important. In accordance with one aspect of the invention, the orthodontic shield 40 is formed from a translucent material so that the color of the underlying teeth of the patient is visible therethrough. In this manner the orthodontic shield is rendered substantially invisible when seen from a distance. The orthodontic shield 40 may also be colored in any particular manner that may be preferred by the patient that will use it. In Some instances the color of the orthodontic shield 40 may be quite prominent if the particular patient wishes to use the orthodontic shield as a fashion statement.

The orthodontic shield 40 is installed on the exterior facing or labial surfaces of the teeth of the patient in the same manner as the orthodontic shield 20 of FIG. 2 is installed on the inwardly facing or lingual surfaces of the teeth of the patient. First, the material of the shield is raised to an elevated temperature either using a conventional home-type microwave or boiling water. In either event, the temperature of the shield at installation should be sufficiently high to render the material thereof malleable, but not so high as to be uncomfortable to the touch of the patient. In this manner any danger of burning the mouth of the patient is completely eliminated.

After the material of the orthodontic shield 40 has been raised to a temperature sufficiently high to render it malleable, the orthodontic shield 40 is pressed into engagement with the outwardly facing or labial surfaces of the patient using finger pressure. In this manner the orthodontic shield 40 is conformed to the shape of the teeth of the patient and to the shape of the orthodontic appliance 30 mounted thereon. Using finger pressure, the orthodontic shield 40 can be conformed to the shape of the teeth and the orthodontic appliance sufficiently that it is retained in the mouth of the patient during daily activities such as diction and eating. Nevertheless, the orthodontic shield is readily removable from the mouth of the patient for cleaning, etc.

Although preferred embodiments of the invention have been illustrated in the accompanying Drawings and described in the foregoing Detailed Description, it will be understood that the invention is not limited to the embodiments disclosed, but is adapted to various modifications and rearrangements of the parts and elements without departing from the spirit of the invention.

I claim:

1. A method forming an orthodontic shield for use in conjunction with an orthodontic appliance mounted on the lingual surfaces of teeth of a patient comprising the steps of:

providing a strip of thermoplastic material having a predetermined length, a predetermined width, and a predetermined thickness;

heating the strip of thermoplastic material sufficiently to render the material thereof malleable under predetermined pressure;

engaging the heated strip of thermoplastic material with the orthodontic appliance and with the adjacent lingual surfaces of the teeth above and below the orthodontic appliance, wherein said shield does not contact the occlusive surface of the teeth of the patient while applying pressure thereto and thereby conforming the strip of thermoplastic material to the configuration of the orthodontic appliance and the adjacent lingual tooth surfaces;

allowing the formed strip of thermoplastic material to cool within the mouth of the patient and thereby forming a snap fit engagement with the orthodontic appliance therein during diction and eating while facilitating removal of the strip of thermoplastic material from the mouth of the patient to facilitate cleaning.

2. The orthodontic shield formed in accordance with the method of claim 1.

3. The method of forming an orthodontic shield of claim 1 wherein the shield has a predetermined color which blends with the color of the adjacent teeth for cosmetic purposes.

4. The method of forming an orthodontic shield of claim 1 wherein the shield has a predetermined prominent color which contrasts with the adjacent teeth and orthodontic appliance for aesthetic purposes.

5. The method of forming an orthodontic shield of claim 1 wherein the shield is formed from translucent material thereby allowing the underlying teeth color to show through the shield.

6. The orthodontic shield formed in accordance with the method of claim 1.

7. A method forming an orthodontic shield for use in conjunction with an orthodontic appliance mounted on the lingual surface of teeth of a patient comprising the steps of:

providing a strip of thermoplastic material having a predetermined length, a predetermined width, and a predetermined thickness;

heating the strip of thermoplastic material sufficiently to render the material thereof malleable under predetermined pressure;

engaging the heated strip of thermoplastic material with the orthodontic appliance and with the adjacent surfaces of the teeth of the patient while applying pressure thereto and thereby forming generally C-shaped indentations having upstanding walls and projecting legs that partially encircle the orthodontic appliance and contact the adjacent lingual tooth surfaces above and below the orthodontic appliance, wherein said shield does not contact the occlusive surface of the teeth;

allowing the formed strip of thermoplastic material to cool within the mouth of the patient and thereby forming a snap fit engagement with the orthodontic appliance therein during diction and eating while facilitating removal of the strip of thermoplastic material from the mouth of the patient to facilitate cleaning.

8. The orthodontic shield formed in accordance with the method of claim 7.

* * * * *